United States Patent [19]

Silverman et al.

[11] Patent Number: 5,455,033

[45] Date of Patent: Oct. 3, 1995

[54] MEDICINAL COMPOSITION FOR TREATMENT OF INFLAMMATION

[75] Inventors: Melvin Silverman; Geneviere DeGree, both of Beverly Hills, Calif.

[73] Assignee: Degree/Silverman M.D. Inc., Beverly Hills, Calif.

[21] Appl. No.: 65,342

[22] Filed: May 21, 1993

[51] Int. Cl.$^6$ .................................................. A61K 35/78
[52] U.S. Cl. ........................... 424/195; 514/934; 514/969
[58] Field of Search .................... 424/195.1; 514/934, 514/969

[56] References Cited

U.S. PATENT DOCUMENTS

| | | | |
|---|---|---|---|
| 4,678,772 | 7/1987 | Segal et al. | 514/25 |
| 5,096,708 | 3/1992 | Gohla et al. | 424/195.1 |
| 5,198,217 | 3/1993 | Vedros | 514/25 |
| 5,215,748 | 6/1993 | Mankovitz | 424/195.1 |
| 5,248,503 | 9/1993 | Emanuel-King | 424/195.1 |

OTHER PUBLICATIONS

Bodinet et al; Planta Med. 59(suppl): A672–A673 (1993).
Pompei et al; Experientia 36(3): 304 (1980).
Do Carmo Lagrota et al; Rev. Microbiol. 14(1): 21–26 (1983).

*Primary Examiner*—Douglas W. Robinson
*Assistant Examiner*—Howard C. Lee
*Attorney, Agent, or Firm*—Poms, Smith, Lande & Rose

[57] ABSTRACT

A medicinal composition for topical application and for use in a method of treatment for genital herpes and other inflammations of the genitalia includes as active ingredients tea tree oil, pau d'arco powder (an extract of lapacho), licorice root extract, and echinacea extract with a local anesthetic, preferably pramoxine hydrochloride. The composition may include soothing ingredients such as aloe vera extract and chamomile extract and is preferably formulated in a cream base.

5 Claims, No Drawings

1

MEDICINAL COMPOSITION FOR TREATMENT OF INFLAMMATION

FIELD OF THE INVENTION

This invention relates to an anti-inflammatory and, in particular, to a medicinal composition useful in the treatment of genital irritations including herpes in its various forms in both men and women.

BACKGROUND OF THE INVENTION

The treatment of various forms of vaginal irritation, itching and discomfort is a crucial part in the office practice of many physicians. Such irritations may originate in bacterial, viral and/or fungal invasions and for a variety of reasons, such irritations are often very difficult to eradicate. Women who are afflicted with genital herpes may suffer extreme discomfort in "breakout" conditions which can last up to at least two to five weeks. Such events can be debilitating and extremely painful.

In addition, irritations and infections can involve a combination of invasive agents including bacteria, virus and fungus types of infections. Treatment of combination infections then can be very complicated in that the treatment agent must not be specific for one infection but rather must be applicable for a more broad spectrum type treatment. Furthermore, there are disease conditions in which the etiology is unknown or at least in which the causal agent has not been isolated and, in such situations, symptomatic treatment at least is desired to promote an alleviation of itching and discomfort as well as rapid healing of lesions.

It is desirable then to identify preferably a topical treatment for genital herpes and other related infections in which the pain and discomfort will be rapidly alleviated and in which healing will be vigorously promoted.

SUMMARY OF THE INVENTION

It has been discovered that a combination of known phylopharmaceutical topical agents in accordance with this invention and in combination with a local anesthetic agent can provide both rapid and effective treatment for a wide variety of genital irritations including genital herpes which will be both long lasting and effective. Furthermore, it has been discovered that the active ingredients in combination herewith produce a synergistic effect vastly superior to the medicinal qualities known in relation to each of the components or derivatives. The active ingredients herein specifically are, in combination, echinacea extract, licorice root extract, an extract of lapacho in powder form, and tea tree oil. The active ingredients are combined with a local anesthetic. The local anesthetic preferred is pramoxine hydrochloride. The active ingredients herein in combination have been found to dramatically treat the systems of a wide variety of disorders upon topical application and, in particular, with genital herpes, have been found to immediately cause a cessation of itching and discomfort with rapid healing. The active ingredients herein are preferably incorporated in a pharmaceutical vehicle of cream base origin but, as will be obvious to those skilled in the art, may be combined in any pharmaceutically acceptable vehicle for topical application.

Accordingly, it is an object of this invention to provide a topical treatment for a wide variety of different irritations, including genital irritations, which is both safe and effective.

It is another object of this invention to provide a medicinal composition in a form for topical application which utilizes over-the-counter medicinal compounds and extracts primarily of a plant origin for eliminating associated itching and discomfort and for quickly healing any lesions associated with the infection.

It is yet another object of this invention to provide a cream medicinal composition for topical application effective against genital herpes in both men and women which uses as active ingredients a combination of four plant extracts with a local anesthetic and a pharmaceutically acceptable base.

It is still another object of this invention to provide a cream base medicinal composition for topical application effective against genital herpes which uses in combination extracts of tea tree oil, echinacea, licorice root, and lapacho (Pau D'Arco powder) and as soothing agents aloe vera extract and chamomile extract with the local anesthetic pramoxine hydrochloride present in effective amounts to both eliminate pain, itching and discomfort, and to rapidly promote healing of any lesions associated with the disease condition.

These and other objects will become readily apparent with reference to the following description:

DETAILED DESCRIPTION

The medicinal composition of this invention incorporates as active ingredients four extracts of plant origin with a local anesthetic. Each of the individual plant-based extracts, as will be subsequently described, is known for having topical medicinal properties both related and unrelated to the treatment of genital herpes. In combination, however, it has been discovered that the medicinal composition is extremely effective against genital herpes and is also effective against a variety of other types of disease conditions of bacterial, viral, or fungal origin. The composition of this invention utilizes over-the-counter available components and extracts and produces a medicinal composition preferably in cream form which will rapidly promote both an end to discomfort and healing upon topical application to involved areas of the human body.

The following is a detailed description of the four extracts of plant base used in the composition of this invention.

Echinacea extract is derived from Echinacea angustifolia De Candolle. In the United States this term is associated with the cone flower and purple cone flower which is a perennial herb native to midwestern states. Echinacea was long known as an Indian medicine and has variously been described as effective against viral infections, to promote wound healing, and to promote increased immune function properties. While the extract was originally thought to be a blood purifier, it has been used in the treatment of snakebite and contains polysaccharide components which have cortisone-like properties in wound healing. The extract also contains inulin which is an activator in the immune system and the root extract has demonstrated anti-viral activity against influenza, herpes, and vesicular stomatitis viruses. It is further regarded as extremely safe with no reported toxicity.

Tea tree oil is also a well-known antiseptic and medicinal composition. Tea tree oil has been used for years to fight infections, both fungus and bacterial, and has been documented as an anti-infectious, anti-fungus, and antiseptic oil. It has been used in treatment of fungal infections, infected ulcers and sores, cold sores, rashes, genital herpes, genital pruitis, and low immune system conditions.

Licorice root extract has also been documented as an anti-inflammatory, anti-viral and anti-allergic composition. Licorice root has been used for soothing peptic ulcers, bladder ailments, and kidney ailments. It also is a remedy for arthritis due to its anti-inflammatory properties, and it has been found to stimulate the production of both cortisone and aldosterone which help reduce inflammation. Of the known ingredients, glycyrrhizin is a glucuronic acid derivative of the terpene, glycyrrhetinic acid. This is known for its anti-inflammatory activity to reduce swelling and edema. A second known compound therein is carbenoxolone. This compound possesses activity against herpes viruses and has been shown to be effective in healing ulcers and erosions of mucous membrane. In addition, it has been found to be effective against gingivostomatitis and recurrent herpes labialis. It generally increases the mucosal blood flow and raises the level of cytoprotective prostaglandins.

Lapacho is derived from a tree native to Brazil, *Tabebuia avellanedae*. The extract from the bark is commonly used although an extract of the heartwood is known. The major components are 16 quinones and lapachol, the latter is known to have anti-microbial and anti-viral activity. This latter isolate has been used in anti-tumor treatment both orally and parenterally and has exhibited anti-parasitic and anti-inflammatory activity. For example, tampons soaked in an alcoholic extract of lapacho have been shown to be very effective against a wide range of inflammations, such as cervicitis and cervicovaginitis.

The last ingredient which is regarded as essential is a local anesthetic for relatively immediate relief from the itching and discomfort which is associated with the various types of irritations which occur in the genital area. It is preferred to use the local anesthetic pramoxine hydrochloride, although other local anesthetics known can be substituted.

In addition, in a preferred embodiment, two soothing ingredients are added. Specifically, aloe vera extract and chamomile extract. The latter when applied to the skin in dermatitis or excema is known to exert an anti-inflammatory and soothing action. In aroma therapy it has been found to have a calming and sedative effect and has been found to be beneficial for the relief of headaches, irritability, migraine and insomnia. These ingredients then are preferred in that a patient suffering from, for example, genital herpes typically will also be facing depression and the related symptoms. The soothing and calming effects of these components then facilitate the healing process.

The table below is a formulation of the preferred medicinal composition of this invention with column A being the preferred composition and column B listing ranges of ingredients. In the table, and throughout the present specification, reference to parts and percentages are by weight unless otherwise indicated.

TABLE

|  | A (Formula D) | B |
| --- | --- | --- |
| Phase #1 |  |  |
| Water | 29.75% |  |
| Glycerin | 1.00% |  |
| Allantoin | 0.60% |  |
| Propylene Glycol | 9.00% |  |
| Methylparaben | 0.20% |  |
| Propylene Glycol | 9.00% |  |
| Methylparaben | 0.20% |  |
| Phase #2 |  |  |

TABLE-continued

|  | A (Formula D) | B |
| --- | --- | --- |
| Glyceryl Stearate (and) PEG-100 Stearate | 8.00% | 0.10%–15.00% |
| Cetyl Alcohol | 6.00% | 0.10%–10.00% |
| Propylparaben | 0.10% |  |
| Triethanolamine | 0.30% | 0.01%–01.00% |
| Aloe Vera Extract | 1.00% | 0.01%–15.00% |
| Chamomile Extract | 2.00% | 0.01%–15.00% |
| Butylparaben | 0.05% |  |
| Tea Tree Oil | 10.00% | 0.01%–55.0% |
| Pramoxine Hydrochloride | 2.00% | 0.01%–25.00% |
| Pau D'Arco Powder (Lapacho) | 10.00% | 0.01%–55.0% |
| Licorice Root Extract | 10.00% | 0.01%–55.0% |
| Echinacea Extract | 10.00% | 0.01%–55.0% |

The "Phase #1" and "Phase #2" form a conventional pharmaceutically acceptable cream vehicle for topical application. These phases may be substituted by any other known pharmaceutically acceptable vehicle. Preferably, the cream vehicle constitutes up to about 45 weight percent of the composition, with the remaining components combining to form the balance of the composition.

In order to formulate the medicinal composition of this invention using the above ingredients, Phase #1 is heated to about 75° C. and Phase #2 is separately heated to about 75° C. Phase #2 is then added to Phase #1 with mixing at 75° C. for about 30 minutes to emulsify. Then while slow mixing, the composition is cooled to about 45° C. whereupon the remaining ingredients are added in the order listed above and thoroughly mixed.

The resulting composition has a pH of 5.5+/−0.5, a viscosity of 50,000+/−10,000, and a specific gravity of 0.980+/−0.005.

The following are sample results of human testing of the compositions of this invention as set forth in the above table.

Patient No. 1 was a 49 year old black female with a history of herpes for 13 years. Breakouts of herpes would normally last from 2 to 5 weeks and were associated with pain, burning, itching and ulcerated sores. Herpes lesions were found at various vulvar locations. This patient was treated with "Formula D", the above composition of this invention, which stopped the pain and itching almost immediately with the lesions healing in several days.

Patient No. 2 was a 35 year old black female with a history of recurrent herpes at or near menstruation. These breakouts were accompanied by severe pain and typical vulvar papules were present followed by ulceration. "Formula D" was applied and the patient felt it was an instantly cool and soothing. Used on an as necessary basis, the patient recovered sufficiently to return to work.

Patient No. 3 is a 22 year old Caucasian female with a 7-month history of herpes. Breakouts usually occurred when the patient was tired or nervous and the patient exhibited marked discomfort and foul odor associated with the herpes breakouts. Typical Herpetic lesions of vulvar were present with a definite odor to the discharge. "Formula D" was applied and the offensive odor associated with the herpes disappeared after the first or second treatment as did the burning sensation.

Patient No. 4 is an 18 year old Caucasian female, 6 weeks pregnant, with a history of herpes. Irregular breakouts of herpes lesions occurred for two years prior to treatment at various sites which resulted in severe irritation. The lesions were ulcerated and some papules were present. "Formula D"

was applied and the irritation was definitely relieved after the first application. With subsequent applications, the lesions healed without pain.

Patient No. 5 was a 35 year old black female who for 3½ years prior to treatment had recurrent Herpetic breakouts. The Herpetic lesions were sufficiently painful that the patient had difficulty in walking or sleeping. The pain was not relieved by applying Cortisone or Zovinax ointment. Herpetic lesions were present involving the clitoris with associated perioral edema. "Formula D" was applied and gave rapid relief in less than five minutes from the debilitating pain. Continued treatment controlled the pain and the lesions healed.

Patient No. 6 was a 28 year old Caucasian female who had periodic breakouts around the vaginal orifice. The patient complained of marked itching and burning in the areas of the breakouts and the diagnosis of herpes was confirmed on culture. Typical papular Herpetic lesions were present. The application of "Formula D" gave the patient relief from the itching and burning within minutes after application. The patient repeated applications as needed and always experienced cessation from the pain and discomfort as lesions healed.

Patient No. 7 was a 22 year old Caucasian female with a history of herpes breakouts for three years previous to treatment. Breakouts were found to be more frequent before and after menstrual periods. The patient experienced severe pain that made it difficult for her to move about normally. When the pain was very severe, she could not go to work, and analgesics such as Tylenol with codeine did not relieve the pain. A physical examination showed lesions with considerable swelling. Treatment with "Formula D" to the lesions in a few minutes caused the lesions to be less swollen and the severe pain which had become unbearable was gone within about ten minutes.

Patient No. 8 is a 19 year old Caucasian female with a recent history of herpes who complained of pain and difficulty in urination. History of painful urination was associated with hesitancy for the past two days. A physical examination revealed herpetic lesions in the periurethral area with marked ulceration and edema. "Formula D" was applied and the severe pain abated in approximately ten minutes and after the second application two hours later, the patient was able to move more easily and without discomfort. On reexamination the next day, the lesions showed a marked decrease in the inflammatory response.

Patient No. 9 is a 30 year old Caucasian female with a 6-year history of recurrent herpes breakouts prior to treatment. She experienced prodromal symptoms before breakouts. The patient therefore knew when a herpes breakout was imminent. The patient had just started to break out with lesions in the left vaginal fourchette. "Formula D" was applied and it immediately took away the discomfort and arrested the breakout. With subsequent use, the patient found that if she applied "Formula D" as soon as she felt the symptoms, she soon felt better and the treat stopped or ameliorated any herpes breakout.

Patient No. 10 was a 22 year old Caucasian female with a history of recurrent herpes breakouts triggered by stress. The patient suffered with severe depression with herpes recurrences. Examination revealed a Herpetic lesion in the right labia majora. "Formula D" was applied and it not only helped to relieve the discomfort of herpes, in addition, the scent from the composition exhibited a calming effect on the patient so that she became more relaxed with a better positive attitude.

In summary then, the combination of plant related medicinal compositions herein has been found to provide an excellent topical treatment for genital herpes and for other related disease conditions. The four extracts combined herein with a local anesthetic are typically also combined with extracts of aloe vera and chamomile extract to provide a more soothing composition in combination with a pharmaceutically acceptable vehicle for topical application.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

We claim:

1. A method of treating genital herpes (HSV-II) comprising:

topically applying to affected genital areas of the human body, a medicinal composition comprising tea tree oil, lapacho extract, licorice root extract, and echinacea extract, each of which is present in an amount of from 0.01 to about 55 weight percent, and from 0.01 to about 25 weight percent of a local anesthetic in a pharmaceutically acceptable vehicle for topical application.

2. The method of treatment of claim 1 wherein the medicinal composition further comprises a soothing effective amount of aloe vera extract and chamomile extract.

3. The method of treatment of claim 1 wherein the local anesthetic is pramoxine hydrochloride.

4. The method of treatment of claim 1 wherein each of the tea tree oil, lapacho extract, licorice root extract, and echinacea extract is present in an amount of from 0.01 to about 25 weight percent.

5. The method of claim 1 wherein the vehicle is a cream vehicle comprising in combination water, glycerin, allantoin, propylene glycol, methylparaben and glyceryl stearate (PEG-100 Stearate), cetyl alcohol, propylparaben, triethanolamine and, as a preservative, butylparaben.

\* \* \* \* \*